US009222901B2

(12) United States Patent
Lauridsen et al.

(10) Patent No.: US 9,222,901 B2
(45) Date of Patent: *Dec. 29, 2015

(54) X-RAY DIFFRACTION METHOD OF MAPPING GRAIN STRUCTURES IN A CRYSTALLINE MATERIAL SAMPLE, AND AN X-RAY DIFFRACTION APPARATUS

(71) Applicants: Danmarks Tekniske Universitet, Lyngby (DK); CARL ZEISS X-RAY MICROSCOPY, INC., Pleasanton, CA (US)

(72) Inventors: Erik Mejdal Lauridsen, Harlev (DK); Stefan Othmar Poulsen, Copenhagen (DK); Peter Reischig, Leicestershire (GB)

(73) Assignees: Danmarks Tekniske Universitet Anker Engelundsvej, Lyngby (DK); CARL ZEISS X-RAY MICROSCOPY, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/198,062

(22) Filed: Mar. 5, 2014

(65) Prior Publication Data
US 2014/0307854 A1    Oct. 16, 2014

Related U.S. Application Data

(63) Continuation-in-part of application No. 13/785,755, filed on Mar. 5, 2013.

(51) Int. Cl.
*G01N 23/20*    (2006.01)
*G01N 23/207*   (2006.01)
*G01N 23/205*   (2006.01)

(52) U.S. Cl.
CPC ........... *G01N 23/207* (2013.01); *G01N 23/205* (2013.01); *G01N 2223/3306* (2013.01);
(Continued)

(58) Field of Classification Search
CPC .............. G01N 23/205; G01N 23/207; G01N 2223/056; G01N 2223/602; G01N 2223/603; G01N 2223/605; G01N 2223/607; G01N 2223/648; G01N 2223/649
See application file for complete search history.

(56) References Cited

U.S. PATENT DOCUMENTS

3,903,415 A    9/1975    Holzapfel
5,008,911 A    4/1991    Harding
(Continued)

FOREIGN PATENT DOCUMENTS

WO    WO 2011/003408 A1 *  1/2011  ............. G01N 23/04
WO    2014063002 A1    4/2014

OTHER PUBLICATIONS

Johnson, G. et al., "X-ray Diffraction Contrast Tomography: A Novel Technique for Three-dimensional Grain Mapping of Polycrystals. II. The Combined Case," Journal of Applied Crystallography, vol. 41, pp. 310-318, Jan. 16, 2008.

(Continued)

*Primary Examiner* — Thomas R Artman
(74) *Attorney, Agent, or Firm* — Sughrue Mion, PLLC

(57) ABSTRACT

An X-ray diffraction method of mapping grain structures in a polycrystalline material sample, where an X-ray detector detects spots or line-shaped segments from beams diffracted from at least some of the grains. A processing device analyzes values received from the X-ray detector and identifies at least the position of the spots or line-shaped segments. The processing device discretizes an initial three-dimensional model of the polycrystalline material sample into voxels and reconstructs the grains in the model by iterative testing associating crystallographic orientations of the voxels to the detected spots or line-shaped segments.

22 Claims, 5 Drawing Sheets

(52) U.S. Cl.
CPC .... *G01N2223/605* (2013.01); *G01N 2223/606* (2013.01); *G01N 2223/607* (2013.01); *G01N 2223/648* (2013.01); *G01N 2223/649* (2013.01)

(56) References Cited

U.S. PATENT DOCUMENTS

| | | |
|---|---|---|
| 5,193,104 A | 3/1993 | Bastie et al. |
| 5,491,738 A | 2/1996 | Blake et al. |
| 2014/0112433 A1 | 4/2014 | Feser et al. |

OTHER PUBLICATIONS

Knapic, M., "X-ray Diffraction Contrast Tomography," University of Ljubljana, Dept. of Physics, 13 pgs., May 28, 2011.

Robach, O. et al., "A tunable multicolour rainbow filter for improved stress and dislocation density field mapping in polycrystals using X-ray Laue microdiffraction", Acta Crystallograpy, vil. 98, No. 2, Mar. 1, 2013.

Guinier, A. et al., "Sur Deux Variantes de la Methode de Laue et Leur Applications", Journal of Applied Crystallography, 1949, pp. 133-138, vol. 2.

Guinier, A. et al., "Researches on the Polygonization of Metals", Progress in Metal Physics, 1950, pp. 177-192, vol. 2.

Ludwig, W. et al., "X-ray diffraction contrast tomography: a novel technique for three-dimensional grain mapping of polycrystals. I. Direct beam case", Journal of Applied Crystallography, 2008, pp. 302-309, vol. 41.

Matthias Stockmeier, et al., "A focusing Laue diffractometer for the investigation of bulk crystals", Journal of Applied Crystallography, 2008, pp. 754-760, vol. 41.

Moscicki, M. et al., "Friedel-pair based indexing method for characterization of single grains with hard X-rays", Materials Science and Engineering A, 2009, pp. 64-68, vol. 524.

Ludwig, W. et al., "Three-dimensional grain mapping by x-ray diffraction contrast tomography and the use of Friedel pairs in diffraction data analysis", Review of Scientific Instruments, 2009, pp. 033905-1 to 033905-9, vol. 80.

Lynch, P. et al., "A laboratory based system for Laue micro x-ray diffraction", Review of Scientific Instruments, Feb. 2007, vol. 78.

Hoffmann, F. et al., "High energy transmission micro-beam Laue synchrotron X-ray diffraction", Material Letters, Mar. 2010, pp. 1302-1305, vol. 64.

\* cited by examiner

X-RAY DIFFRACTION METHOD OF MAPPING GRAIN STRUCTURES IN A CRYSTALLINE MATERIAL SAMPLE, AND AN X-RAY DIFFRACTION APPARATUS

CROSS-REFERENCE TO RELATED APPLICATIONS

This is a Continuation application which claims priority based on U.S. Utility patent application Ser. No. 13/785,755 filed Mar. 5, 2013, the contents of all of which are incorporated herein by reference in their entirety.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

In a first aspect the present invention relates to an X-ray diffraction method of mapping grain structures in a crystalline material sample, where an X-ray source provides a polychromatic X-ray beam in a beam path, in which beam path the polychromatic X-ray beam is divergent, a staging device positions the crystalline material sample in the beam path, and an X-ray detector detects a plurality of diffracted X-ray beams leaving the crystalline material sample.

The article "A focusing Laue diffractometer for investigation of bulk crystals" by Matthias Stockmeier and Andreas Magerl, Journal of Applied Crystallography (2008), 41, 754-760, describes a method of this kind where the crystalline material sample is a single crystal. It is well-known that diffraction of X-rays by a crystal occurs when Bragg's equation is fulfilled, $\lambda=2*d*\sin\theta$, where $\lambda$ is the wavelength of the X-ray, d is the spacing of the crystal lattice planes causing diffraction, and $\theta$ (called the Bragg angle) is the angle between the X-Ray beam and the lattice plane. The source provides a polychromatic X-ray beam including many different wavelengths, which for any given position of the sample in relation to the source provides a high probability for actual diffraction from the single crystal. In addition the beam path is divergent and consequently at each point on the sample the X-rays impinge with a different Bragg angle, varying from $\theta_{min}$ to $\theta_{max}$, and this variation range of the Bragg angle is determined by the geometry of the set-up, namely the distance from the source to the sample and the size of the sample in combination with the divergence of the X-ray beam. The article describes a focussing effect obtained when the detector is at a distance from the sample corresponding to the distance from the source to the sample while at the same time the diffracting planes are perpendicular to the surface of the single crystal. The focussing effect occurs in the scattering plane and causes the diffracted X-ray beam to hit the detector as a substantially two-dimensional line-shaped segment oriented perpendicular to the scattering plane.

U.S. Pat. No. 3,903,415 discloses diffraction measurements in a set-up using an X-ray source providing white (polychromatic) X-ray radiation. Pinhole diaphragms are located in the X-ray beam path to collimate the beam into a parallel beam before it reaches the sample. A lead plate is located behind the sample. The lead plate has a circular opening allowing X-ray radiation diffracted by the sample at a predetermined angle to pass on to a detector located behind the lead plate, whereas other X-ray radiation is blocked by the lead plate.

U.S. Pat. No. 5,491,738 discloses an X-ray diffraction apparatus having a beam source providing a collimated X-ray beam being preferably monochromatic. The non-collimated beam from the X-ray source is divergent, and a collimator with a pinhole makes the beam line-shaped and parallel before it reaches the sample. If the X-ray beam is polychromatic, then the detector is designed to measure the distribution of X-ray diffraction photons within one selected energy range, or within some selected energy ranges.

The article "X-ray diffraction contrast tomography: a novel technique for three-dimensional grain mapping of polycrystals. Part 1: direct beam case", Journal of Applied Crystallography (2008), 41, 302-309 describes application of a monochrome synchrotron X-ray beam to illuminate a sample. With X-ray diffraction contrast tomography the grains of a polycrystalline material sample are imaged using an occasionally occurring diffraction contribution to the X-ray attenuation coefficient in the non-diffracted X-ray beam leaving the crystalline material sample. The analysis is thus using the information detected in the direct beam path. Each time a grain fulfils the Bragg diffraction condition a diffraction contrast occurs. The diffraction contrast appears on the detector behind the sample as an extinction spot caused by a local reduction of the transmitted beam intensity recorded on the detector. In the article, the three-dimensional grain shapes are reconstructed from a plurality of projections using algebraic reconstruction techniques (ART). The procedure for the three-dimensional grain shape reconstruction is based on spatial filtering criteria only, and the procedure can therefore be performed without analysing the grain orientations. With respect to grain orientations the article specifies that the intensity of the diffractions spots must be included in order to determine orientations, and even with integrated intensities several solutions may exist and choices have to be made. It is explained in the article that overlapping diffraction contrasts present a problem and that the sample consequently had to have only little grain orientation spread, grains of approximately the same size and tailored transverse sample dimensions in order to limit the probability of spot overlap.

Considerable efforts have been put into the development of techniques for three-dimensional grain mapping of polycrystalline materials. These techniques are utilizing monochromatic, parallel X-ray beams from a synchrotron facility and employ reconstruction algorithms of the kind known in tomography in order to provide a non-destructive characterization of a sample of polycrystalline material.

An example of utilizing monochromatic, parallel X-ray beams from a synchrotron facility is given in the article "Three-dimensional grain mapping by x-ray diffraction contrast tomography and the use of Friedel pairs in diffraction data analysis" by W. Ludwig et al., Review of Scientific Instruments, 80, 033905 (2009). The method used in this article is based on X-ray diffraction contrast tomography, where the grains of a polycrystalline material sample are imaged using a occasionally occurring diffraction contribution to the X-ray attenuation coefficient in the non-diffracted X-ray beam leaving the crystalline material sample. This analysis using the information detected in the direct beam path is supplemented with analysis of the diffracted beams, and in a full 360° rotation of the sample the Bragg angle is fulfilled a maximum of four times. Each set of lattice planes may thus give rise to four diffraction spots, which make up two pairs, where the spots in the pair are separated by a 180° rotation of the sample. The analysis relating to the pairs is based on the fact that the monochromatic X-ray beam has a known wavelength which simplifies the Bragg equation. The diffraction spots observed are of irregular shape and the intensity of the spots may be used to facilitate matching of the pairs. With respect to implementation in practise the article observes that using a computing cluster of 50 nodes, a data set comprising of 1000 grains could be analysed in one day. With a monochromatic, parallel X-ray beam it is thus a heavy processor task to obtain a result.

BRIEF SUMMARY OF THE INVENTION

It is a purpose of the present invention to provide a reliable acquisition and calculation of data from a complex crystalline material sample.

The initially mentioned X-ray diffraction method according to the present invention includes the steps of:
the crystalline material sample is a polycrystalline material sample having a plurality of grains,
the staging device locates the polycrystalline material sample in a plurality of mutually different angular positions in relation to the X-ray source,
the X-ray detector detects spots or line-shaped segments from beams diffracted from at least some of the grains, each spot having a position and each line-shaped segment having a position and a length,
a processing device analyses values received from the X-ray detector and utilizes at least the positions of the spots or line-shaped segments when determining a three-dimensional model of the polycrystalline material sample, and
wherein the processing device discretizes an initial three-dimensional model of the polycrystalline material sample into voxels and reconstructs the grains in the model by iterative testing associating crystallographic orientations of the voxels to the detected spots or line-shaped segments.

The illumination of a polycrystalline material sample results in a large number of diffractions, and illumination by a divergent polychromatic X-ray beam further increases the number of diffractions. The prior art deals with either a polycrystalline material sample illuminated by a monochromatic, parallel beam, or a single crystal illuminated by a polychromatic X-ray beam. In both cases data handling is time consuming and requires significant processor capacity. According to the present invention a polycrystalline material sample is illuminated with a divergent polychromatic X-ray beam, and there is thus obtained a high number of diffractions in a short time, because each grain can cause diffractions, and because the polychromatic X-ray beam triggers significantly more diffractions than a monochromatic beam, and because the divergence of the beam also adds to the number of diffractions as the beam encompass a range of Bragg angles illuminating the sample at the same instant. It is thus possible to make a significant rotation of the polycrystalline material sample from one image to the next, and yet obtain the required diffraction data from the plurality of grains in the sample, and the lower number of images required for determining the three-dimensional model of the polycrystalline material sample, compared to a method utilising monochromatic X-rays, results in faster data acquisition and in a significantly faster data processing.

By detecting line-shaped segments from beams diffracted from the grains, where each line-shaped segment has a position and a length, the data handling is simplified as the data analysed are more unique in their information than traditional diffraction spots. Diffraction spots cover a large area per spot on the detector, and overlapping of spots from different diffraction events is a real concern making it largely impossible to process data from many simultaneous diffraction events. Line-shaped segments on the other hand are simpler to analyse than spots, and many more lines than spots can be detected on the detector without confusing one diffraction event with another diffraction event.

The processing device discretizes an initial three-dimensional model of the polycrystalline material sample into voxels and reconstructs the grains in the model by iterative testing associating crystallographic orientations of the voxels to the detected line-shaped segments. This may have the advantage of providing robust data also in cases with a level of noise in the detected signals. Due to the high amount of diffraction data in a single image, as little as 100 to 200, or 50 to 100 images, may be fully adequate to determine the three-dimensional model of the polycrystalline material sample. The low number of images is an advantage as the amount of data to be processed is reduced. The low number of images required for a full representation of the sample also provides the advantage of faster processing of the sample.

It is preferred that the processing device establishes a first table associating voxels with detected spots or line-shaped segments. The first table can be used in evaluation of the validity of the association of voxels to detected spots or line-shaped segments and to select the associations having high validity. The selected associations represent a reduced data set, and the selection is a step in the iterative testing associating crystallographic orientations of the voxels to the detected spots or line-shaped segments. In a second step in the iterative testing the processing device may again discretize the model of the polycrystalline material sample into voxels of smaller size and/or higher precision in the orientation.

Preferably, each voxel is associated with a directional vector pointing from the voxel to the individual detected spot or line-shaped segment. Such associations can be calculated for each voxel in a simple manner, and the processing can be carried out in parallel for different voxels.

Vectors can be represented in various manners, however it is preferred that the directional vector used to associate a voxel with a detected spot or line-shaped segment is represented in a stereographic projection, as this provides a compact data set.

The validity of the association of voxels to detected spots or line-shaped segments can be calculated out from geometrical conditions, which however may require considerable processing power. It is preferred that the processing device for the individual voxel in the first table compares the detected spots or line-shaped segments with pre-calculated sets of possible spots or line-shaped segments. By using the pre-calculated sets the processing of the validity becomes a mere comparison of data sets, and such comparison is fast and does not put heavy demands on computing power.

Preferably, the processing device uses a second table associating voxels with pre-calculated sets of possible spots or line-shaped segments at positions on the detector. The second table can be a stored table accessed by the processing device, or it can be a table prepared by the processing device based on a stored table and information on the type of crystalline material in the sample. By using the second table the processing device need not pre-calculate the sets to be used in assessing the validity of the detected data, because the processing device can then simply read the already pre-calculated data from the second table. Thus, the testing performed by the processing device may suitably involve comparing the detected spots or line-shaped segments at positions on the detector with pre-calculated sets in the second table.

It is preferred that at least some of the line-shaped segments are paired as originating from diffractions from the same grain and the positions of the paired line-shaped segments are used in determining the position of this grain within the three-dimensional model of the polycrystalline material sample. The length of the paired line-shaped segments may also be used in determining a width of this grain. The pairing of line-shaped segments originating from diffractions from the same grain provides an efficient singling out of distinct information from a multitude of information caused by the many diffraction events occurring for the polycrystalline sample illuminated by the polychromatic, divergent X-ray beam. The length of the line-shaped segment may be used when segments are paired, because segments originating from diffractions from opposite sides of the same lattice plane have the same length when detected on the same detector. From a data handling perspective it is well-known and rather simple and thus fast to analyse line-segments and find the line-segments sharing common properties.

Pairing of the spots or line-shaped segments originating from diffractions from the same grain can be utilized to determine the grain position of this grain within the polycrystalline material sample. The paired spots or line-shaped segments can be analysed by relating their positions to a curve path intersecting the grain position. Combining multiple instances of such paired spots or line-shaped segments originating from a single grain improves the data on the grain position in the polycrystalline material sample. In this manner it is possible with a high degree of probability to obtain the position of the individual grains in the sample. In addition the length of the paired line-shaped segments is used in determining a width of this grain, and this geometric information allows a faster and more precise determination of the three-dimensional characteristics of the polycrystalline material sample.

In an optional method at least two pairs of spots or line-shaped segments originating from diffractions from the same grain are used in determining the grain position of this grain within the three-dimensional model of the polycrystalline material sample. Analysis of the position of the spots or line-shaped segments constituting the pairs provides information on the grain position in a three-dimensional space. Although the mapping procedure of building a model of the polycrystalline material sample can be performed by using a single pair of segments, there is preferably used two, three or more pairs of segments for building a model of the polycrystalline material sample in order to make the procedure more precise and robust. It is also possible to use many pairs, such as more than 8 pairs.

When determination of the orientation of grains is desired, then one possibility is to base the determination of orientation on the intensity of diffraction spots. With the method according to the present invention it is also possible to determine the crystallographic orientation of the grains by having the processing device identify the orientation of the individual line-shaped segment, and by using the orientation of the line-shaped segment in determining the crystallographic orientation of the grain associated with the line-shaped segment. An advantage of using the orientation of the line-shaped segment is that it is quickly obtained, both when it comes to exposure time and when it comes to processing of the calculations.

It is typically a desire not only to determine grain positions but also to obtain information on the three-dimensional morphology of the grains. It is preferred that a shape reconstruction of the grains is performed. The shape reconstruction makes use of the length of the paired line-shaped segments to provide the width of the grain in one direction. Combination of multiple such widths gives approximate information on the three-dimensional grain shape. In order to perform a more detailed reconstruction it is preferred that in addition to segment detection of line-shaped segments originating from diffractions, spot detection is performed of diffraction spots representing two-dimensional projections of grain morphology. The spot detection provides information on the shape of the grain boundary. The spot is a two-dimensional projection of the shape of the three-dimensional grain, and this provides information improving the precision of the reconstruction. It is furthermore possible to combine details coming from adjacent grains for improving the reconstruction.

When spot detection is performed it is preferred that the segment detection occurs at a first distance between sample and detector, and spot detection occurs at a second distance between sample and detector, where the second distance is preferably at least the double of the first distance. The detection at the first distance is for line-segments, and these represent one width of grain, but the grain shape in the direction perpendicular to the length of the segment is not apparent. The advantage of making the second distance for spot detection at least the double of the first distance is that the size of the spots increases with increasing distance and magnification of the grain size above natural size is desirable. Spot detection may occur at shorter distances, but then the spot size will appear smaller.

It is preferred that the processing device uses the position and possibly the length and possibly the orientation, but optionally not the intensity, of the line-shaped segments when these are paired as originating from diffractions from the same grain. The intensities of the segments are coupled to the X-ray source spectrum and are not as easy to distinguish as the length or the position or the orientation of the segment. And image analysis based on intensities typically requires longer exposure time in order to provide useful data, so it is an advantage to both image acquisition and data processing when the intensity is not required in order to obtain the desired results.

In a second aspect, the present invention also relates to an X-ray diffraction apparatus for mapping grain structures in a crystalline material sample, comprising an X-ray source for emitting a polychromatic X-ray beam in a divergent beam path, a staging device for positioning the sample in the beam path in a plurality of mutually different angular positions in relation to the X-ray source, and an X-ray detector for detecting at least diffracted X-ray beams leaving the sample, which X-ray detector has at least a first position in which the detector is at a distance from the sample corresponding to in the range of 80-120% of the distance from the X-ray source to the sample. According to the second aspect of the present invention the apparatus further comprises a diaphragm located between the X-ray source and the sample in the beam path, which diaphragm allows a central portion of the divergent beam to illuminate the crystalline material sample and prevents beam portions outside the central portion from illuminating the detector, and a processing device for analysing values received from the X-ray detector(s) and for utilizing at least the positions of the line-shaped segments in the determination of a three-dimensional model of the polycrystalline material sample, and wherein the processing device uses positions of the line-shaped segments in determining the crystallographic orientation of the grain associated with the line-shaped segments.

The diaphragm restricts the size of the divergent beam to the size relevant for illuminating the sample, and the diaphragm cuts off any remaining outer portions of the beam from illuminating the detector. On the detector there is consequently an image of the sample in the divergent, direct beam path, but outside of this image of the sample the detector remains unaffected by the direct beam and thus free to detect diffracted beams. This facilitates the image handling of the diffracted beams because there is no need to compensate for illumination from the direct beam. The processing device identifies at least the position and the length of the individual line-shaped segments and pairs at least some of the line-shaped segments as originating from diffractions from the same grain. The advantages of such segment identification and pairing are explained in the above description of the method. Reference is also made to the above explanation of advantages of using the length of the paired line-shaped segments in determining a width of this grain.

In an embodiment the processing device is adapted to identifying at least a position and a length of individual line-shaped segments, and is adapted to pairing at least some of the line-shaped segments as originating from diffractions from the same grain, and is adapted to using the length of the paired line-shaped segments in determining a width of this grain.

In a further embodiment the processing device may use the orientation of the line-shaped segment in determining the crystallographic orientation of the grain associated with the line-shaped segment. In a further embodiment the apparatus includes a filter device for reducing the frequency range of the polychromatic X-ray beam. This embodiment may be useful when there is a desire to operate with only some out of all possible diffractions from the polychromatic X-ray beam and the polycrystalline material sample. The polychromatic X-ray beam is in principle "white" covering the broad range of frequencies (wavelengths), but the intensity level typically depends on the frequency and intensity peaks may occur at certain frequencies. One possibility of reducing the frequency range is to filter off frequencies outside these high-energy frequencies, another possibility is to filter off frequencies outside a continuous frequency band, and a third possibility is to filter off frequencies based on the crystallographic properties of the material sample. The filter device reduces the number of diffractions appearing on the detected images, and thus makes it simpler to analyse the detected data. However, in the general case it is not necessary to use a filter device.

In one embodiment the X-ray detector has a second position in which the detector is at a distance from the sample corresponding to in the range of 200-1000% of the distance from the X-ray source to the sample, preferably from 250-600% of the distance from the X-ray source to the sample. When the detector is at a distance from the sample of from two to ten times the distance from the X-ray source to the sample then the grains have a size that makes the grain contour and thus the grain boundary projected onto the detector more visible in detail. The intensity of the spot is reduced as the distance increases, and it is consequently—as a balance between suitable size and acceptable intensity—preferred that the detector distance is in the range of 250-600% of the distance from the X-ray source to the sample.

Instead of using one detector in two different distances, it is possible to use a first detector and a second detector, where the second X-ray detector is positioned in a second position in which the second detector is at a distance from the sample corresponding to in the range of 200-1000% of the distance from the X-ray source to the sample, preferably from 250-600% of the distance from the X-ray source to the sample.

BRIEF DESCRIPTION OF THE SEVERAL VIEWS OF THE DRAWING

In the following, illustrative examples and embodiments of the present invention are described in further detail with reference to the schematic drawings, on which

DETAILED DESCRIPTION OF THE INVENTION

Figure 2:
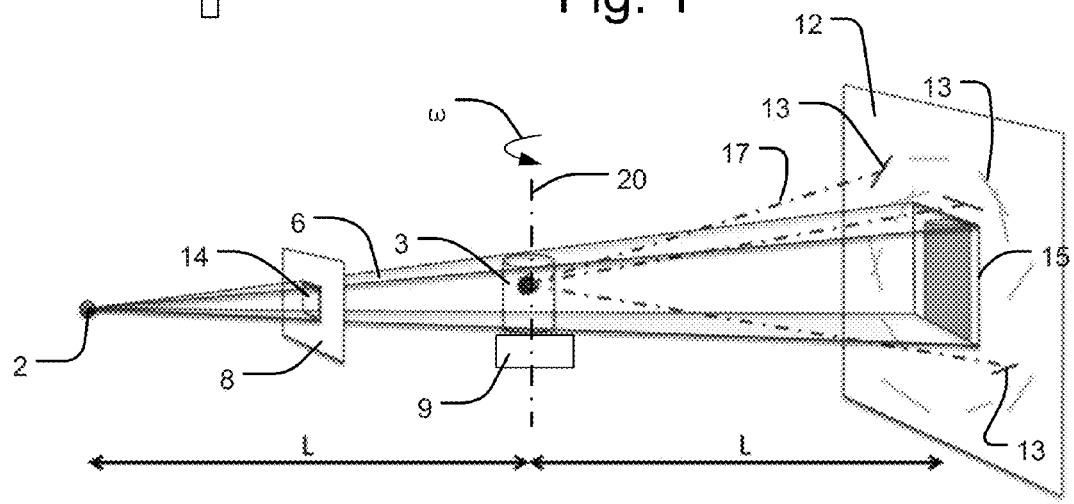
FIG. 2 illustrates an apparatus according to the invention.
Figure 7:
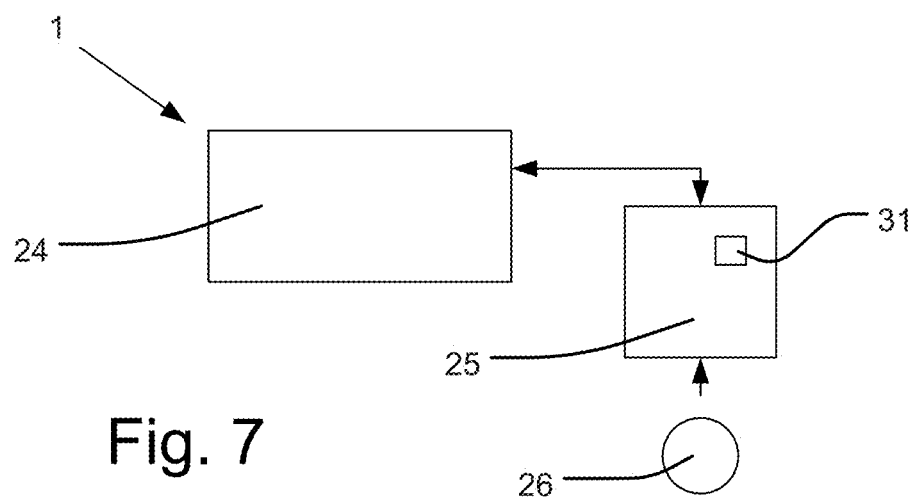
FIG. 7 illustrates an apparatus according to the present invention.

An embodiment of an X-ray diffraction apparatus is generally denoted 1 in FIG. 7 and it has a data acquisition unit 24 and a data analysing unit 25 that may be operated by a human operator 26. The data acquisition unit comprises an X-ray source 2, a staging device 9 and a first detector 12, and as illustrated in FIG. 2 these parts are located with the source at one side of the staging device and the detector at the other side thereof.

The X-ray source 2 provides a polychromatic X-ray beam 6 in a beam path. The beam is preferably passed through a pinhole opening in a diaphragm in the source 2, which pinhole opening is much smaller than the dimensions of the beam at the staging device 9, so that source 2 can be considered a point source. The X-ray source is a so-called laboratory X-ray source, and such a source is very different from a synchrotron X-ray source used for mapping grain structures in a polycrystalline material. The synchrotron source is a giant structure that provides a monochrome X-ray beam in a parallel beam. The X-ray source 2 is in comparison a very small structure that may have a maximum outer dimension of 10 meters or less. Laboratory X-ray sources may be of the type having an X-ray tube, in which electrons are accelerated in a vacuum by an electric field and shot into a target piece of metal. X-rays are emitted as the electrons decelerate in the metal. The output spectrum has a continuous spectrum of X-rays with sharp peaks in intensity at certain energies depending on the kind of metal used for the target, such as copper, tungsten, silver, rhodium or molybdenum. The X-ray source 2 may also be of a laser type or of another available laboratory type. Such X-ray sources are e.g. available from suppliers such as Lyncean Technologies, Inc., Palo Alto, Calif., USA; Xradia Inc., Concord, Calif., USA; Proto Manufacturing Ltd., Ontario, Canada; SkyScan, Kontich, Belgium, and Phoenix X-ray, Wunstorf, Germany; and Gatan, Calif., USA. For example, an XuM X-ray UltraMicroscope from Gatan may be utilized as X-ray source, when modified with detectors etc. as described in the following.

The beam from the X-ray source 2 may pass through one or more optional components (not shown) conditioning the beam, such as condensers, filters, attenuators, etc. as may be suitable for the particular set-up for analysing a specific sample. Such components are considered part of the X-ray source 2, unless otherwise explained in the following description.

Figure 1:
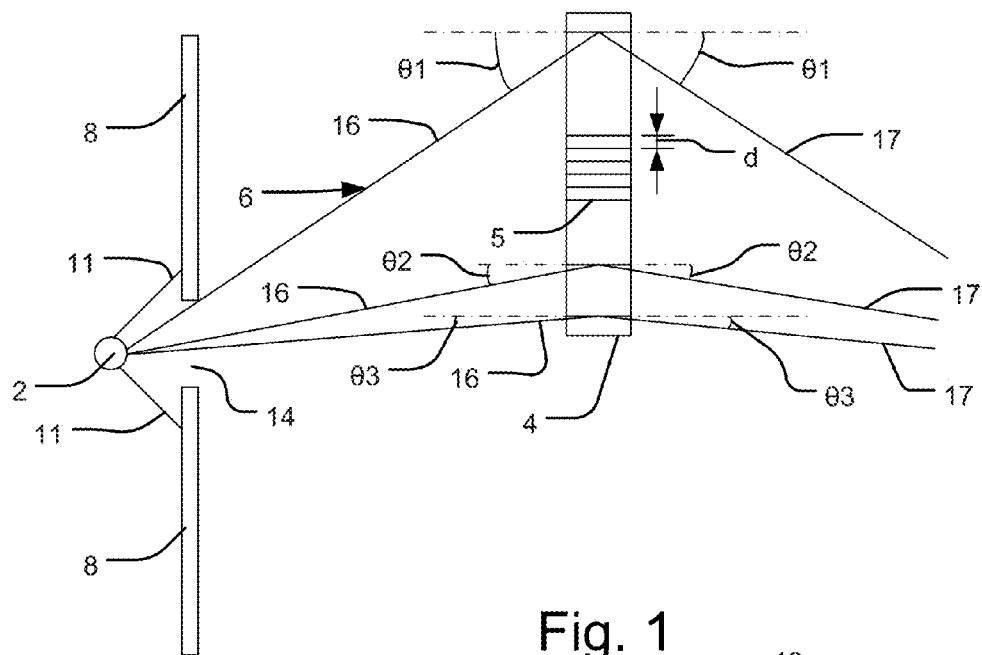
FIG. 1 illustrates diffraction in a grain in a crystalline material illuminated by a divergent X-ray beam in an apparatus and a method according to the present invention.

The polychromatic X-ray beam 6 is divergent in the beam path. The divergent beam has the effect that the X-rays illuminating a crystalline material sample 3 on the staging device 9 are not parallel, but follow a straight line from the source 2 to the illuminated point on the sample. This is illustrated in more detail in FIG. 1. A crystalline grain 4 has a plurality of parallel lattice planes 5, each separated by a distance d, which is the spacing of the crystal lattice planes in the grain. The X-ray diffracted at the upper crystal plane has an incident angle $\theta 1$ with the crystal plane and an equal diffracted angle $\theta 1$, whereas the X-ray diffracted at the lowermost crystal plane has an incident angle $\theta 3$ with the crystal plane and an equal diffracted angle $\theta 3$, and an incident X-ray 16 diffracted at an intermediate crystal plane has an incident angle $\theta 2$ with the crystal plane and an equal diffracted angle $\theta 2$ for a diffracted X-ray 17. It appears from the illustration that $\theta 1$ is the largest angle, $\theta 3$ is the smallest angle and $\theta 2$ is an angle of intermediate size. The angles correspond to $\theta$ in Bragg's equation $\lambda = 2*d*\sin \theta$, and if d is considered constant for the lattice planes in the illuminated crystal grain 2 then the wavelength of the X-ray diffracted at $\theta 1$ is slightly different from the wavelength of the X-ray diffracted at $\theta 3$.

The X-ray beam 6 is divergent in the direct beam path (undiffracted X-rays) and could in principle illuminate the complete area of the first detector 12. However, it is an advantage if the divergent beam is restricted to approximately illuminating the crystalline material sample 3, or the portion thereof to be analysed. The direct beam illuminating the sample results in a direct beam image area 15 on the first detector. A diaphragm 8 positioned between the source 2 and the sample 3 restricts the cross-sectional size of the X-ray beam. The diaphragm 8 has a beam opening 14 allowing the divergent beam to pass through and onwards to the sample 3, but the X-rays 11 hitting the diaphragm 8 outside of beam opening 14 are stopped by diaphragm 8. The area of the first detector outside the direct beam image area 15 is thus reserved for detection of diffracted X-ray beams. These blocked X-rays are prevented from illuminating the first detector. Portions of the X-rays that would hit the diaphragm 8 outside of beam opening 14 may be acted upon by a condenser device provided at the source so that they are directed through beam opening 14. Such condensing of the X-ray beam acts to concentrate the beam to the useful area and to an increase in the intensity of the beam.

On the sample 3 the X-rays impinge with a Bragg angle varying from $\theta_{min}$ to $\theta_{max}$, and this variation range of the Bragg angle is given by the distance between the source 2 and the sample 3, and the size of the illuminated sample, provided that the beam opening provides for full illumination of the sample. If less than the full size of the sample is illuminated then the size of beam opening 14 and the distance from sample 2 to beam opening 14 may limit the values of $\theta_{min}$ and $\theta_{max}$.

The size of beam opening 14 may be adjustable, and the position of diaphragm 8 may also be adjustable. The distance between the source 2 and sample 3 is denoted L. The position of diaphragm 8 is adjustable within this distance L, and the distance between diaphragm 8 and source 2 is preferably in the range from 0.2-0.99 L, and more preferably in the range from 0.3-0.8 L. The diaphragm needs to be rather large if it is positioned close to the sample 3, but if it is positioned close to the source 2 then there is required a higher degree of precision in the size of the beam opening and the centring of the diaphragm. Diaphragm 8 can be provided as a set of diaphragm plates having differently sized beam openings, and the diaphragm plate with the suitable size for a given sample 3 can be chosen when the sample is to be mapped. Alternatively, a diaphragm plate can have displaceable shutter members that define the beam opening and are set in position according to the size of the actual sample 3 to be mapped. Beam opening 14 may have any suitable shape, such as rectangular, circular, or oval. The shape of beam opening 14 may also be adjustable in order to match the actual shape of the actual sample 3. If the sample is of elongate shape, then the beam opening may suitably be of a corresponding shape.

The staging device 9 is adapted to position and rotate the crystalline material sample 3 in the path of X-ray beam 6. A staging device is well-known in X-ray diffraction techniques, and it comprises a material sample holder and a stage for adjusting and rotating the material sample. The stage may be motorised and may also be translated transversely out of the beam path in order to acquire reference images of the beam profile. The stage has a central, rotational axis 20 and the position of the stage can be adjusted so that this rotational axis 20 is perpendicular to the central portion of the X-ray beam. The stage can rotate the crystalline material sample 3 about rotational axis 20 in stepwise, incremental rotational movements that may be settable such as in the range from 0.01° to 15° per incremental rotation. During image capture the stage maintains the sample 3 stationary in the fixed rotational position. The stage has a default reference point for the rotational position of 0°, and preferably also a possibility for setting an actual reference point at initiation of the rotational movement of a mounted material sample. The current rotational angle w of the stage with respect to the reference point is communicated from the staging device 9 to a processing device or to a data memory in such a manner that the rotational angel is associated with the image detected on the first detector 12. As an example, a staging device and sample holder may be obtained from the firm Bruker AXS GmbH, Karlsruhe, Germany.

It is preferred that the incremental rotation between the individual image positions is in the range from 1° to 15°, and more preferably between 3° to 12°. With an incremental rotation of e.g. 4°, 90 images are taken during the full 360° rotation of the sample. Although it is possible to obtain the diffracted signals with as little as 24 images separated by incremental rotations of 15°, or 30 images separated by incremental rotations of 12°, the 90 images provides some redundant information that may used in the analysis.

The first detector 12 is positioned in the direct path of the X-ray beam 6. The first detector has a two-dimensional detector screen capable of detecting X-rays. The screen orientation is preferably so that the surface of the two-dimensional flat screen of the first detector is about perpendicular to the centre line of the beam 6. As one example out of many possible, the first detector 12 may be a camera with a detector of the type charge-coupled device (CCD) or a fluorescent screen coupled to a CDD.

When a diffraction occurs in a crystal grain a part of the intensity of X-ray beam 16 is scattered (directed) in another direction, namely in direction of line 17. Due to the diffraction some of the intensity of the direct X-ray beam in the area covered by the grain has been removed from the direct beam for the particular wavelength involved in the diffraction, but the polychromatic nature of the X-ray beam from the source 2 causes the majority of the beam intensity in the direct beam path to continue to the first detector and illuminate the same in the direct beam image area 15. There is consequently not any visible extinction spot as would have been the case if the X-ray beam had been monochromatic.

Figure 6:
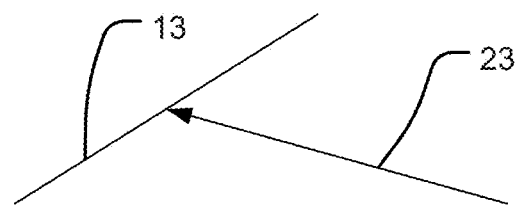
FIG. 6 illustrates a position of a line-shaped segment.

The diffracted X-ray 17 continues to the first detector where the X-ray is detected as a line-shaped segment 13. The crystalline material sample 3 is polycrystalline and for each fixed rotational position of the sample several or many of the grains may cause diffraction and a plurality of line-shaped segments 13 may be detected on the first detector at different positions on the first detector. The position of the line-shaped segment 13 can be given by a directional vector 23 providing the position of e.g. the middle of the segment as illustrated in FIG. 6. Some of the line-shaped segments may happen to be at about the same position on the first detector, but such line-shaped segments almost always have different orientations and thus appear on the detector as crossing line segments. At least one image is recorded for each fixed rotational position of the sample. The images are stored in an image library, such as a memory in a processing unit in the apparatus 1.

If the average grain size of the polycrystalline material is very small, such as 20 μm, the line-shaped segments appear like spots on the first detector, because the line length is very small, and in case the polycrystalline material is in a deformed state the lines become broad and look more like spots. A processing device 31 in the data analysing unit 25 (FIG. 7) analyses the individual image in a so-called segmentation process where each discernible line-shaped segment 13 is identified and the position and the length of the segment are determined, and preferably also the orientation of the segment. Such information on each detected line-shaped segment is stored in a database DB together with the information from the staging device 9 on the corresponding rotational angle ω of the staging device. The segmentation and storage in the database are illustrated in the flow chart illustrated in FIG. 8.

Figure 3:
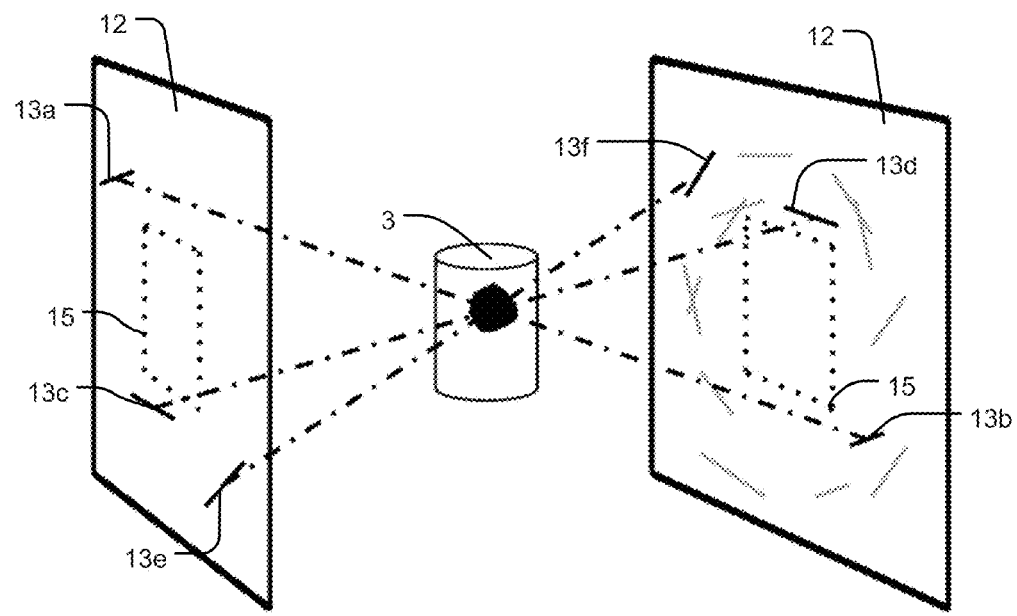
FIG. 3 illustrates paired line-shaped segments according to the method.

In a subsequent mapping process the processing device analyses the data in order to determine the position of the individual grain within a three-dimensional geometric model of the crystalline material sample 2. Some of the line-shaped segments can be paired as originating from the grain, and such pairing may facilitate the mapping. The pairing is based on the observation that during a full 360° rotation about rotational axis 20, diffractions from the lattice plane 5 in one grain may occur four times for a single diffraction order, which make up two pairs, where the line-shaped segments in the pair are separated by a 180° rotation of the sample 3. The 180° rotation is simply because the front side of a lattice plane and the back side of the same lattice plane can both cause diffraction. When a pair of images taken at rotational angle $\omega_i$ and at rotational angle $\omega_{i+180}°$ is set up in the coordinate system of sample 3 they appear as illustrated in FIG. 3. The pairs of line-shaped segments are easily detectable because they have the same length and the approximate same orientation and have positions that are correlated by being positioned on a line passing through the sample 3. In the mapping procedure the processing device can quickly find line-shaped segments having the same length and the approximately same orientation, and from this sub-set of line-shaped segments it is easy to determine which two segments can be paired as being positioned on a common line extending through the sample 2. Once the pairs of line-shaped segments have been identified, the line connecting the segments is also known, and it is known that the grain is located on this line. It is possible to build the model of the polycrystalline material sample 3 based on a few pairs of line-shaped segments per grain, but the mapping process is more precise and robust when more pairs of line-shaped segments can be located for the individual grain as the lines have different orientations in space and all cross through the grain. In FIG. 3 a first pair is illustrated as 13a, 13b, and a second pair is illustrated as 13c, 13d, and a third pair is illustrated as 13e, 13f.

A single grain 4 typically has a plurality of lattice planes. Lattice planes can be identified by Miller indices, and a grain with e.g. a fcc crystal structure (face-centred-cubic) have at least the lattice planes (111), (200), (220) and (311), and each of these lattice planes can cause pairs of line-shaped segments. It is preferred that the mapping process uses at least three pairs of line-shaped segments in the determination of the three-dimensional location of the grain within the polycrystalline material sample.

Due to the high number of diffractions from a single grain and the well-defined geometrical relationship of crystal planes relevant for the individual grain it is possible to base the pairing of line-shaped segments on other factors than two segments placed on a straight line, which is relevant when the two segments are from images taken at rotational angle $\omega_i$ and at rotational angle $\omega_{i+180}°$. The pairing can thus be based on images taken with other rotational angles, such as $\omega_i$ and $\omega_{i+90}°$. It is also possible to perform pairing of line-shaped segments based on the different lattice planes pertaining to a single grain. Such a pairing involves information of the actual crystal structure of the grains (fcc, bcc etc.) in the sample 3. When a sample is analysed, the alloy is known and the crystal structure is also known, and the mapping procedure can thus be based on some known facts relating to the crystallographic type, relevant lattice planes and other information, like the physical size and the approximate number of grains.

Figure 4:
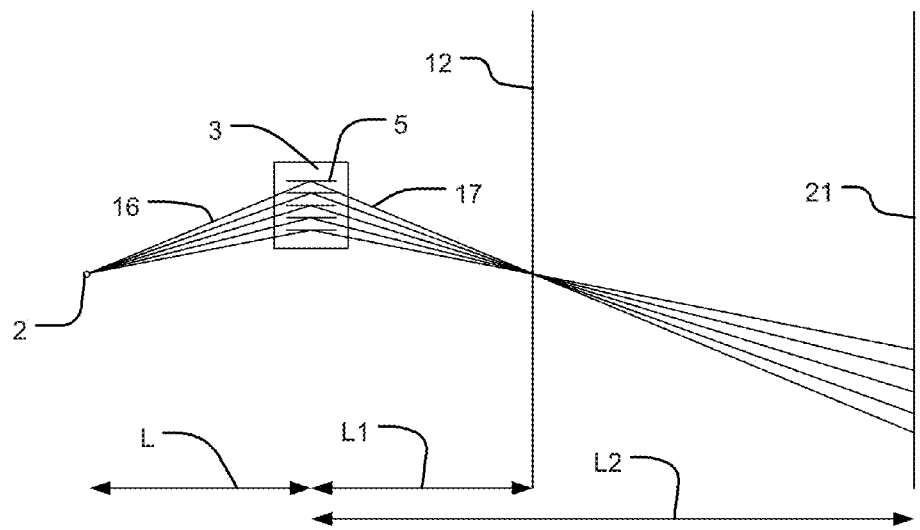
FIG. 4 illustrates distances between sample and detector.

The paths of incident X-rays 16 and diffracted X-rays 17 are illustrated in FIG. 4 where L designates the distance between the X-ray source 2 and the crystalline material sample 3, and L1 designates the distance between the crystalline material sample 3 and the first detector 12. The divergent nature of the X-ray beam is apparent on the left-hand side of sample 3, and on the right hand side of the sample the diffracted X-rays 17 are seen to be convergent to a focus position at the distance L1=L and then to proceed in a divergent beam to the right hand side of the focus position. The illustration in FIG. 4 is simplified and the first detector is illustrated as positioned in a distance L1 from the sample 3 corresponding to the distance L between the sample 3 and the source 2. At this distance the line-shaped segments will occur, but they will also occur when the first detector is in other positions. When the lattice planes in the grain are not parallel with the centre line of the X-ray beam then the focusing distance for the line-shaped segment is different from L, and it is consequently preferred that the first X-ray detector has a first position in which the detector is at a distance from the sample 3 corresponding to in the range of 80-120% of the distance from the X-ray source 2 to the sample 3. With the first detector position in this range the line-shaped segments can be detected.

A second detector 21 shown in FIG. 4 is located at the distance L2 from the sample 3. L2 is different from L1, and on detector 21 the diffracted X-ray beams 17 provide a spot of two-dimensional shape. The spot is a two-dimensional projection of the three-dimensional grain morphology and provides information on the shape of the grains boundary. The size of the spot increases as the distance L2 increases in comparison to L. When L2 equals 200% of L the spots correspond to the natural size of the grains, and when L2 is larger than 200% of L a magnification of the spot size occurs. It is preferred that L2 is at least 250% of L such as up to 600% of L. In an embodiment of the apparatus 1 the distance L from source 2 to sample 3 is in the range from 5 mm to 200 mm, and the range from 20 mm to 40 mm is preferred. The distance L is preferably adjustable in order to adapt the set-up to the specific sample, such as to the size and morphology of the sample.

As an alternative to using a second detector 21, the position of the first detector 12 can be adjustable and a set of images can be acquired with the first detector in the first distance L1, and then the first detector can be located in the distance L2 from the sample and a further set of images can be acquired. It is also possible to use well-known zooming optics to vary the effective pixel resolution at position L1 and/or position L2.

Figure 5:
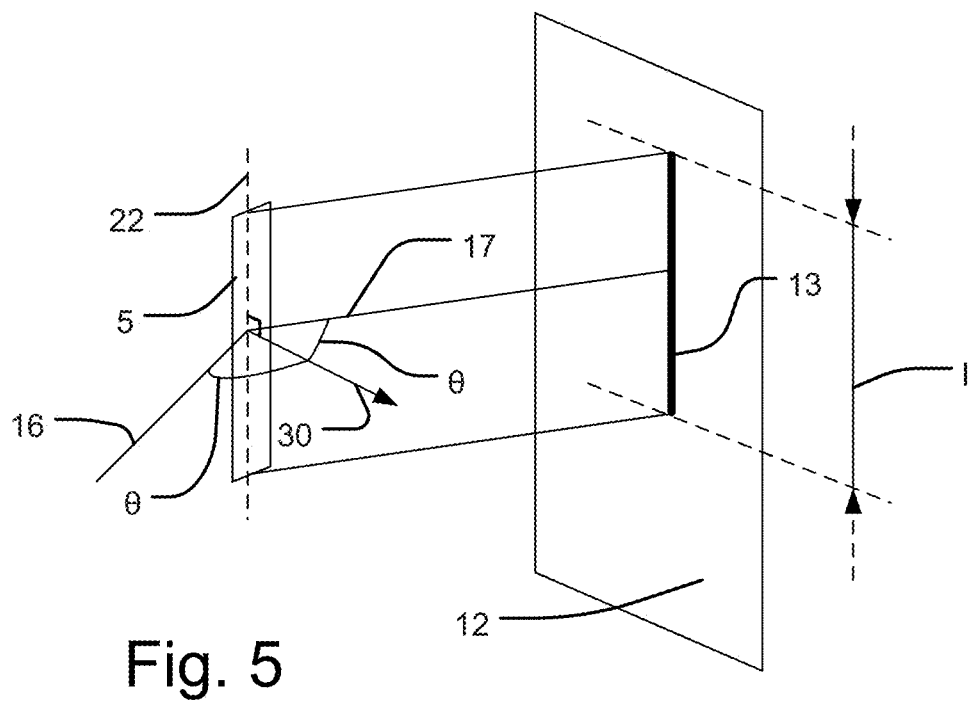
FIG. 5 illustrates the length of a line-shaped segment.

When the first detector is in the focus position at the distance L1 and the line-shaped segment 13 appears on the detector with a length l, as illustrated in FIG. 5, this length is representative of a width of the grain, namely to the calliper width given by the maximum width of the grain along the direction of the lattice planes causing the diffraction. In FIG. 5 the incident X-ray 16 and the diffracted X-ray 17 each forms the Bragg angle θ with a scattering vector 30. The scattering vector is orthogonal to the lattice plane, and the incident X-ray 16, the diffracted X-ray 17 and the scattering vector 30 form a common plane. The lattice plane 5 has a width along a line 22 orthogonal to said common plane, and the length of the line-shaped segment corresponds to this width. The length of the line-shaped segment 13 can thus be used in determining a width of the grain when the grain shape is reconstructed.

Figure 8:
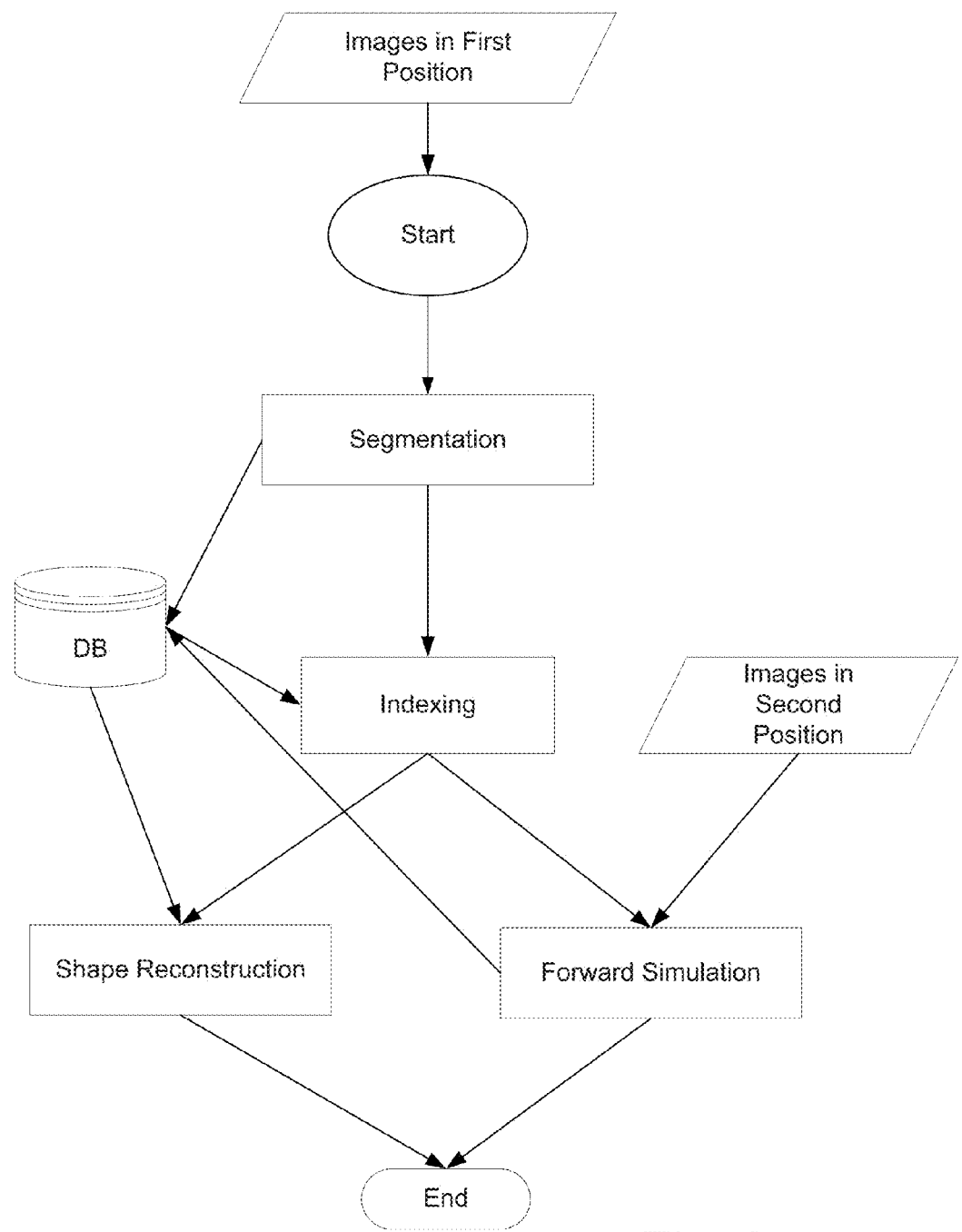
FIG. 8 is a flow diagram illustrating one example of method steps.

The flow chart of FIG. 8 illustrates that images are acquired with the detector in the first position at the distance L1, and optionally images may also be acquired with the detector in the second position at the distance L2. After the images have been acquired the segmentation process is initiated, and information on the segments are stored in the database DB. As described in the above, a mapping process is then performed, and the three-dimensional geometrical positions of the individual grains are determined.

In a following process the three-dimensional geometric shapes of the grains are determined. Each grain is associated with many diffraction events, and for the individual diffraction event there is—from the length l of the line-shaped segment—known information on the width of the grain in a specific direction, and this provides two points located on the surface of the grain. In the shape reconstruction this information is added for all diffraction events pertaining to the grain and thus a model of the three-dimensional grain shape is obtained in a comparatively fast process.

The orientation of the line-shaped segment 13 is directly related to the orientation of the lattice plane 5, and this information can be applied in an indexing process to the model of the three-dimensional grain so that also the crystal orientation is given.

If a better precision of the tree-dimensional grain shape is desired, then images obtained with a detector in the second distance L2 can be utilized to provide more details on the actual shape of grain boundaries. The individual diffraction event causing a line shape in the first detector position at L1 will in the second detector position at L2 be positioned in the same relative position on the detector, because the deflected X-ray follows a straight line. The divergence of the X-ray beam 6 causes the spot to be larger when the distance L2 is larger. Each spot is a two-dimensional projection of the three-dimensional grain shape, and the contour of the grain can be determined from the many diffraction events associated with the grain.

The spots on the images acquired at the distance L2 and/or L1 may also be used in forward simulation where the indexing data of grain positions provide information on the center of mass for the grains and the orientation of the grains. Such forward simulation can preferably be based on the indexing data, but can also utilize a simple brute-force approach where crystal orientations are assigned to sample positions according to e.g. a Monte Carlo optimisation. In the forward simulation different simulations of grain shapes and grain orientations are compared with the detected spots in an iterative process that refines the accuracy of the three-dimensional grains shapes in the model. The forward simulation demands more processing capacity, and results in a model where the true three-dimensional morphology of the grain structure may be determined. It is a well-known advantage of the forward simulation that it can compensate for noise in the measurements and it can fill out gaps in the detected data. Information on the grain shape from the forward simulation can be added to the database and be utilized to e.g. correct for errors or missing data in the indexing.

The first detector 12 and the second detector 21 may be of the same type, or the one detector may have less spatial resolution and larger field-of-view than the other detector. The resolution of the detector may e.g. be in the range of 2 to 200 micro-meters, when it is of the charge-coupled device (CCD) type, or it may be of higher or lower resolution according to the desired detail of the material samples to be analysed.

The mapping of grains may also be performed in a forward simulation where an initial three-dimensional model of the polycrystalline material sample is made. The outline of the polycrystalline material sample is discretizes into voxels, where each voxel is geometrically smaller than the smallest gain in the material sample. The grains are then reconstructed in the model by iterative testing where crystallographic orientations are associated to the voxels, and the diffractions from such orientations are compared with the actually detected line-shaped segments, and the orientations providing matching with the detected line-shaped segments are selected.

An example of processing involving discretizing a model of a sample and reconstruction of grains in the model by iterative testing associating crystallographic orientations of the voxels to the detected spots or line-shaped segments is described in further detail.

This example of the method aims at reducing the processing power required for performing the calculations required for reconstruction. The method is applicable to a setup where the detector detects spots or line-shaped segments with the detector located at about the distance L1, and the method is also applicable to a setup where the detector is at another distance, such as the distance L2, where spots are detected. The method is also applicable to a setup detecting spots or line-shaped segments at one distance and spots at another distance. An advantage of using detection of spots or line-shaped segments in the focus plane is that the noise level is typically lower than at other distances, and another advantage is the possibility of also utilizing the orientation of the line-shaped segments in the detector plane. When line-shaped segments are detected calculations may be simplified by using the two end points of the line in the calculations.

A model of the sample is discretized into voxels. The size of the voxels may initially be chosen to correspond to or be smaller than the average grain size in the sample. When smaller voxels are used the precision and reliability is higher, but computation time increases as more calculations are to be performed. The model may cover a larger size than the actual sample, but in that case there will not be results for the voxels located outside the area of the sample. As an example, the model may have 200×200×200 voxels, which may also be seen as 200 layers of a voxel grid of 200×200.

Each voxel in the model is associated with an orientation grid. The orientation grid includes a data representation of a set of directional vectors which vectors point from the voxel to points or line-shaped segments. The individual directional vector can be represented in space by two angles, and one possibility of discretizing the orientation space is to divide a 360° circle with a spacing of about 0.5° and to divide an orthogonal half circle from +90° to −90° with a spacing of about 0.5°.

For a given crystal lattice structure, such as fcc, and a given grain orientation, each crystallographic plane fulfils the Bragg condition multiple times during a full scan of the sample. On a typical setup the first few {hkl} crystallographic plane families are expected to be observed, represented by the plane normal orientation, and potentially any (hkl) plane within that family may be observed.

For a given crystallographic orientation of a grain and for a defined plurality of angular positions used during a full scan of the material sample, it can be pre-calculated which diffractions may theoretically occur. Such pre-calculated diffraction spots may be called the theoretically expected set of diffraction signals. Such pre-calculated set of values can be stored in a second table for all crystallographic orientations of the grain. The pre-calculation can be done before the scanning operation and be stored, or the processing device can perform the pre-calculation during the scan.

It is also possible to prepare a library of pre-calculated second tables pertaining to commonly occurring crystal lattice structures. The processor device may then read the relevant second table from the stored library based on user data input defining the actual crystal lattice structure of the sample.

During the scanning the diffractions observed on the detector or detectors are recorded for the full scan of the sample. In a first table, representing a voxel grid corresponding to the voxels in the model of the sample, each voxel is associated with a set of directional vectors pointing from the voxel to all detected diffractions, and the data set is stored by the processing device.

The experimental data collected in the first table is then compared with the pre-calculated data in the second table. For each voxel the set of experimental data is compared with the pre-calculated sets of theoretical data in the second table, and for the individual set the number of directional vectors matching with the experimental data for the voxel is found. It is simple to calculate a ratio between the number of matching vectors and the number of vectors in the pre-calculated set and to take this ratio as a measure of the correctness. Such a ratio can be stored in a third table, or if desired in the first table or in the second table. When stored, such as in a third table, there is obtained a very compact data set in which, for each voxel, the crystallographic orientations given by the discretized orientation space are associated with the ratio representing the correctness of the particular orientation. It is then easy and fast to scan through the resulting data set in search of the crystallographic orientation having the highest correctness ratio for a given voxel. The crystallographic orientation having the directional vectors pointing to the positions of the detected spots or line-shaped segments with the highest degree of correctness is selected as crystallographic orientation for the voxel in the model.

Based on the positional information and the crystallographic orientation resulting from this first calculation, a second discretizing can be performed with smaller voxel size, such as 500×500×500 voxels, and an orientation grid having an orientation precision in the range of 0.05° to 0.1°. These grids may be filled with data only around the results found in the first calculation, and the greater precision is thus feasible by using a desktop or laptop computer. There may of course be performed more iterations than two.

In an embodiment the processing device is configured, by being programmed, to establish a theoretical model of the sample discretized into voxels, and to discretize the voxels in the model with respect to orientation space, and to compare theoretical diffractions resulting from a possible orientation with detected diffractions, and to determine voxel orientations.

The processing device can be further configured to associate the individual voxel in the model with a set of directional vectors pointing from the voxel to the positions of the detected spots or line-shaped segments.

The processing device can be further configured to establish a pre-calculated set of directional vectors pointing from a common origin to positions of theoretically possible diffraction spots for a defined crystallographic orientation, and to establish such a pre-calculated set for individual crystallographic orientations in a discretized orientation space.

The processing device can be configured to compare many sets of theoretical diffractions with the detected diffractions, each set corresponding to diffractions resulting from a single crystallographic orientation, and the many sets covering many crystallographic orientations. An example of discretizing into voxels is now described in more detail. In order to establish a theoretical model the material sample is discretized into voxels having smaller volume than the average grain size of the material sample. The size of the voxels may be chosen so that in average at least ten or more voxels pertain to one and the same physical grain in the material sample. The theoretical model is then for each voxel discretized with respect to the orientation space. For each possible orientation the resulting theoretical diffractions are compared with the detected line-shaped segments on the first detector and possibly also with diffraction data from the second detector. In this manner it is possible to find the voxel orientations that actually fit to the detected diffraction data, and thus determine the orientation of the grains in the model. With respect to the size of the individual grain, adjacent voxels having similar orientation are considered as belonging to the same grain. As the iterations evolve, voxels are joined and they more and more match the actual grain structure of the polycrystalline material sample. The grain shapes can be further optimized by special methods like Monte Carlo simulations, or Laguerre tessalation codes.

In the mapping and/or reconstruction calculations it is possible to utilize principles from well-known calculation methods, such as the discrete algebraic reconstruction technique (DART), the conventional iterative algebraic reconstruction method (ART), simultaneous iterative reconstruction technique (SIRT), or simultaneous algebraic reconstruction technique (SART).

The method uses images acquired with the detector in the first position at the distance L1, and in a segmentation process data on the line-shaped segments are determined and stored in the database. The forward simulation process is then performed, involving discretization into voxels, and the three-dimensional geometrical positions of the individual grains are determined, and the crystallographic orientations of the grains are determined. The grain shapes may then be further optimized by calculation methods as mentioned, or images acquired at the distance L2 may be used to provide information on the shapes of the grain boundaries. As illustrated in FIG. 8 it is also possible to use forward simulation in combination with shape reconstruction, e.g. so that the forward simulation is used to fill out areas of missing or conflicting data.

It is also possible to perform additional analysis of the diffraction signals from the images acquired at the distance L1 and/or from the images acquired at the distance L2 in order to determine information on the stress state of the grains. As an example a detected line-shaped segment 13 may deviate from a straight shape and this provides information of the local stress state in the grain. As another example, an image detected at the distance L2 may include a so-called K-alpha line and this may be used to associate an observed diffraction signal to a specific X-ray energy. When the X-ray energy is known the wavelength is known, and then a precise value d for the spacing of the crystal lattice planes can be calculated, and this may be utilized for providing information on the stress state of the grain.

Figure 9:
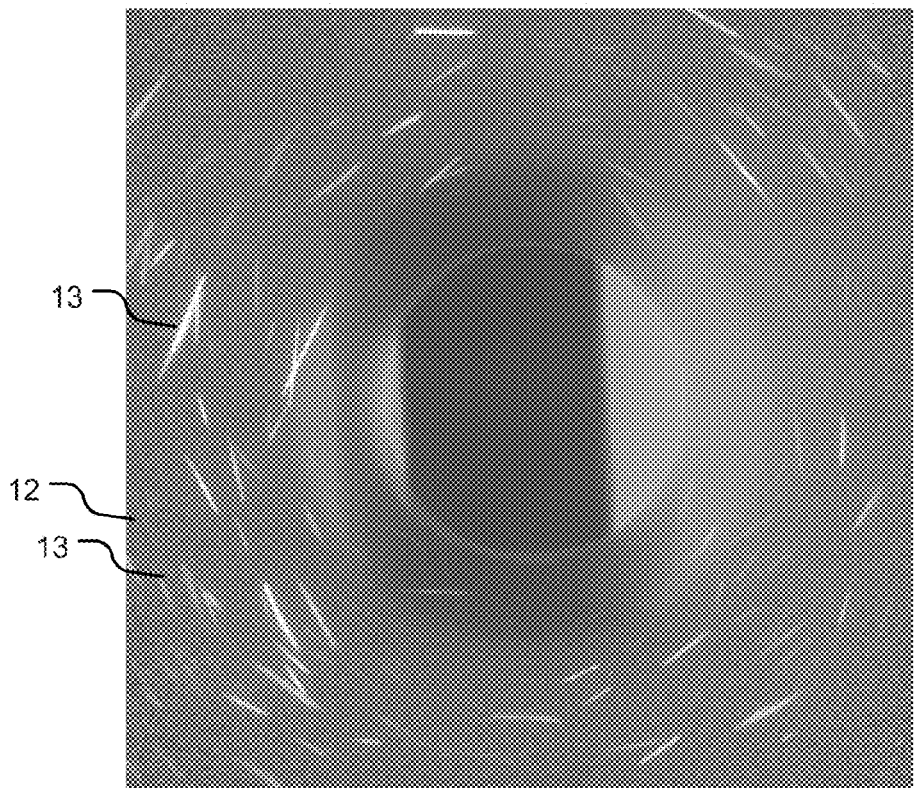
FIG. 9 is an example of an image detected in a first detector position.

An example of an image detected on the first detector 12 at the distance L1 is shown in FIG. 9 where the line-shaped segments 13 are observed as bright lines 13.

Figure 10:
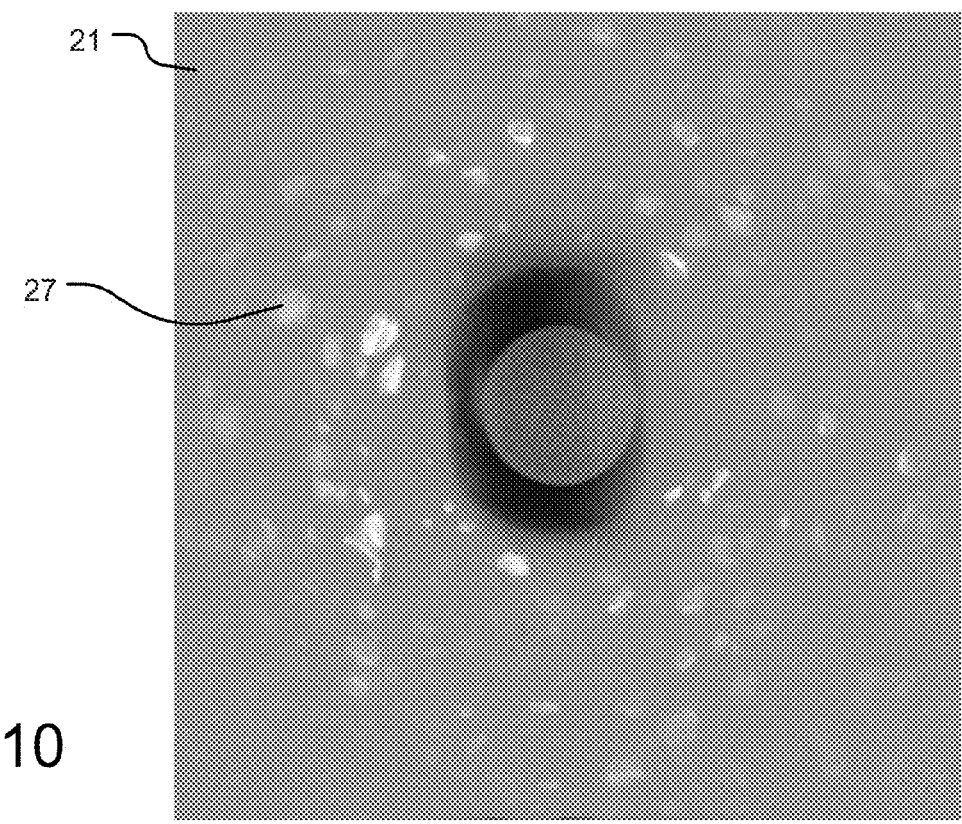
FIG. 10 is an example of an image detected in a second detector position.

An example of an image detected on the second detector 21 at the distance L2 is shown in FIG. 10 where spots 27 are bright. At the centre of the image is seen a projection image of the crystalline material sample 3.

The second detector 21 need not be located at a position in the direct path of the beam 6. The second detector can be located at any position where diffracted signals can be detected. The second detector may as an example be located parallel to the first detector, but shifted sideways to be located asymmetrically with respect to the beam 6. The second detector need not be parallel to the first detector. As an example, the second detector may be located as a plane orthogonal to any radius of the length L2 in a sphere having specimen 3 at the centre of the sphere. It is also possible to use several detectors 21 as the second detector.

The X-ray source 2 may be supplemented with a filter device reducing the frequency range of the polychromatic X-ray beam. The filter device is positioned in the beam path at source 2 or in between source 2 and diaphragm 8. The filter device is typically a sheet of material, like aluminum or silver.

Details from the above-mentioned embodiments and examples may be combined into other embodiments and examples within the scope of the patent claims.

The invention claimed is:

1. An X-ray diffraction method of mapping grain structures in a crystalline material sample, where
   an X-ray source provides a polychromatic X-ray beam in a beam path, in which beam path the polychromatic X-ray beam is divergent,
   a staging device positions the crystalline material sample in the beam path,
   an X-ray detector detects a plurality of diffracted X-ray beams leaving the crystalline material sample, and wherein
   the crystalline material sample is a polycrystalline material sample having a plurality of grains,
   the staging device locates the polycrystalline material sample in a plurality of mutually different angular positions in relation to the X-ray source,
   the X-ray detector detects spots or line-shaped segments from beams diffracted from at least some of the grains, each spot having a position and each line-shaped segment having a position and a length,
   a processing device analyses values received from the X-ray detector and utilizes at least the positions of the spots or line-shaped segments when determining a three-dimensional model of the polycrystalline material sample, and wherein
   the processing device discretizes an initial three-dimensional model of the polycrystalline material sample into voxels and reconstructs the grains in the model by iterative testing associating crystallographic orientations of the voxels to the detected spots or line-shaped segments.

2. The X-ray diffraction method according to claim 1, wherein the processing device establishes a first table associating voxels with detected spots or line-shaped segments.

3. The X-ray diffraction method according to claim 2, wherein each voxel is associated with a directional vector pointing from the voxel to the individual detected spot or line-shaped segment.

4. The X-ray diffraction method according to claim 3, wherein the directional vector used to associate a voxel with a detected spot or line-shaped segment is represented in a stereographic projection.

5. The X-ray diffraction method according to claim 2, wherein the processing device for the individual voxel in the first table compares the detected spots or line-shaped segments with pre-calculated sets of possible spots or line-shaped segments.

6. The X-ray diffraction method according to claim 2, wherein at least two pairs of line-shaped segments originating from diffractions from the same grain are used in determining the grain position of this grain within the three-dimensional model of the polycrystalline material sample.

7. The X-ray diffraction method according to claim 2, wherein the processing device identifies the orientation of the individual line-shaped segment, and uses the orientation of the line-shaped segment in determining the crystallographic orientation of the grain associated with the line-shaped segment.

8. The X-ray diffraction method according to claim 1, wherein the processing device uses a second table associating voxels with pre-calculated sets of possible spots or line-shaped segments.

9. The X-ray diffraction method according to claim 8, wherein the testing performed by the processing device involves comparing the detected spots or line-shaped segments with the pre-calculated sets in the second table.

10. The X-ray diffraction method according to claim 1, wherein at least some of the line-shaped segments are paired as originating from diffractions from the same grain and the positions of the paired line-shaped segments are used in determining the position of this grain with-in the three-dimensional model of the polycrystalline material sample.

11. The X-ray diffraction method according to claim 1, wherein in addition to segment detection of line-shaped segments originating from diffractions, spot detection is performed of diffraction spots representing two-dimensional grain morphology.

12. The X-ray diffraction method according to claim 11, wherein segment detection occurs at a first distance between sample and detector, and spot detection occurs at a second distance between sample and detector.

13. The X-ray diffraction method according to claim 12, wherein the second distance is at least the double of the first distance.

14. The X-ray diffraction method according to claim 1, wherein the processing device uses the position and the length of the line-shaped segments when these are paired as originating from diffractions from the same grain.

15. The X-ray diffraction method according to claim 1, wherein the processing device determines the stress state of individual grains in the polycrystalline material sample.

16. An X-ray diffraction apparatus for mapping grain structures in a polycrystalline material sample, comprising
   an X-ray source for emitting a polychromatic X-ray beam in a divergent beam path,
   a staging device for positioning the sample in the beam path in a plurality of mutually different angular positions in relation to the X-ray source, an X-ray detector for detecting spots or line-shaped segments from beams diffracted from at least some of the grains, each spot or line-shaped segment having a position, which X-ray detector has at least a first position in which the detector is at a distance from the sample corresponding to in the range of 80-120% of the distance from the X-ray source to the sample, wherein a diaphragm is located between the X-ray source and the sample in the beam path, which diaphragm allows a central portion of the divergent beam to illuminate the crystalline material sample and prevents beam portions outside the central portion from illuminating the detector, a processing device configured to analyse values received from the X-ray detector and for utilizing at least the positions of the line-shaped segments in the determination of a three-dimensional model of the polycrystalline material sample, and wherein the processing device is configured to establish a theoretical model of the sample discretized into voxels, and to discretize the voxels in the model with respect to orientation space, and to compare theoretical diffractions resulting from a possible orientation with detected diffractions, and to determine voxel orientations.

17. The X-ray diffraction apparatus according to claim 16, wherein the processing device is configured to associate the individual voxel in the model with a set of directional vectors pointing from the voxel to the positions of the detected spots or line-shaped segments.

18. The X-ray diffraction apparatus according to claim 16, wherein the processing device is configured to establish a pre-calculated set of directional vectors pointing from a common origin to positions of theoretically possible diffraction spots for a defined crystallographic orientation, and to establish such a pre-calculated set for individual crystallographic orientations in a discretized orientation space.

19. The X-ray diffraction apparatus according to claim 16, wherein the processing device is configured to compare many sets of theoretical diffractions with the detected diffractions, each set corresponding to diffractions resulting from a single crystallographic orientation, and the many sets covering many crystallographic orientations.

20. The X-ray diffraction apparatus according to claim 16, wherein the X-ray detector has a second position in which the detector is at a distance from the sample corresponding to in the range of 200-1000% of the distance from the X-ray source to the sample.

21. The X-ray diffraction apparatus according to claim 16, wherein the apparatus has a second X-ray detector positioned in a second position in which the second detector is at a distance from the sample corresponding to in the range of 200-1000% of the distance from the X-ray source to the sample.

22. The X-ray diffraction apparatus according to claim 16, wherein the processing device determines the stress state of individual grains in the polycrystalline material sample.

\* \* \* \* \*